(12) United States Patent
Wüstenbecker

(10) Patent No.: US 12,315,652 B2
(45) Date of Patent: May 27, 2025

(54) X-RAY SHIELDING CABINET

(71) Applicant: Baker Hughes Holdings LLC, Houston, TX (US)

(72) Inventor: Michael Wüstenbecker, Lütjensee (DE)

(73) Assignee: Baker Hughes Holdings LLC, Houston, TX (US)

( * ) Notice: Subject to any disclaimer, the term of this patent is extended or adjusted under 35 U.S.C. 154(b) by 203 days.

(21) Appl. No.: 18/184,491

(22) Filed: Mar. 15, 2023

(65) Prior Publication Data

US 2024/0312662 A1    Sep. 19, 2024

(51) Int. Cl.
*G21K 1/00*    (2006.01)

(52) U.S. Cl.
CPC ........................... *G21K 1/00* (2013.01)

(58) Field of Classification Search
None
See application file for complete search history.

(56) References Cited

U.S. PATENT DOCUMENTS

| | | | |
|---|---|---|---|
| 7,495,247 B2 | 2/2009 | Jorg | |
| 7,891,872 B2 | 2/2011 | Kuhnmuench | |
| 2010/0111266 A1* | 5/2010 | Kuhnmuench | G21F 7/005 378/203 |
| 2012/0140883 A1 | 6/2012 | Iwakiri et al. | |
| 2021/0166828 A1* | 6/2021 | Walker | G21F 3/00 |
| 2023/0182252 A1* | 6/2023 | Nakanishi | B23Q 11/0891 409/134 |

FOREIGN PATENT DOCUMENTS

| | | |
|---|---|---|
| CN | 2500262 Y | 7/2002 |
| CN | 109065200 A | 12/2018 |
| CN | 111272788 A | 6/2020 |

(Continued)

OTHER PUBLICATIONS

Shota Shimizu et al., Visualization of Scattered Radiation Distribution under Various X-ray Room Conditions in Medical Facilities and Development of Its Display Tool, Major in Science and Engineering, Graduate School of Natural Science and Technology, Shimane University (Dec. 28, 2021).

(Continued)

*Primary Examiner* — Hoon K Song
(74) *Attorney, Agent, or Firm* — Mintz, Levin, Cohn, Ferris, Glovsky and Popeo, P.C.

(57) ABSTRACT

An x-ray shielding cabinet includes a housing that at least partially defines a cavity configured to receive and retain an x-ray scanning system. A first door and a second door partially define a side and top of the cavity. A first track supports a first end of the first door and a second track on the supports a second end of the first door. The first door is movable along the first track and the second track. A third track supports a first end of the second door, and a fourth track supports a second end of the second door. The fourth track is parallel to the first track, the second track, and the third track. The second door is movable along the third track and the fourth track. The first and second doors are configured to travel across one another when moving between an open position and a closed position.

18 Claims, 9 Drawing Sheets

(56) References Cited

FOREIGN PATENT DOCUMENTS

| | | |
|---|---|---|
| CN | 114740023 A | 7/2022 |
| GB | 490480 A | 8/1938 |
| JP | 2003161707 A | 6/2003 |
| KR | 100367413 B1 | 1/2003 |
| KR | 100894112 B1 | 4/2009 |
| KR | 101580910 B1 | 12/2015 |
| WO | 01/84558 A1 | 11/2001 |
| WO | 2013/084373 A1 | 6/2013 |

OTHER PUBLICATIONS

Extended European Search Report dated Nov. 15, 2024, Application No. 24158574.4, 17 pages.

\* cited by examiner

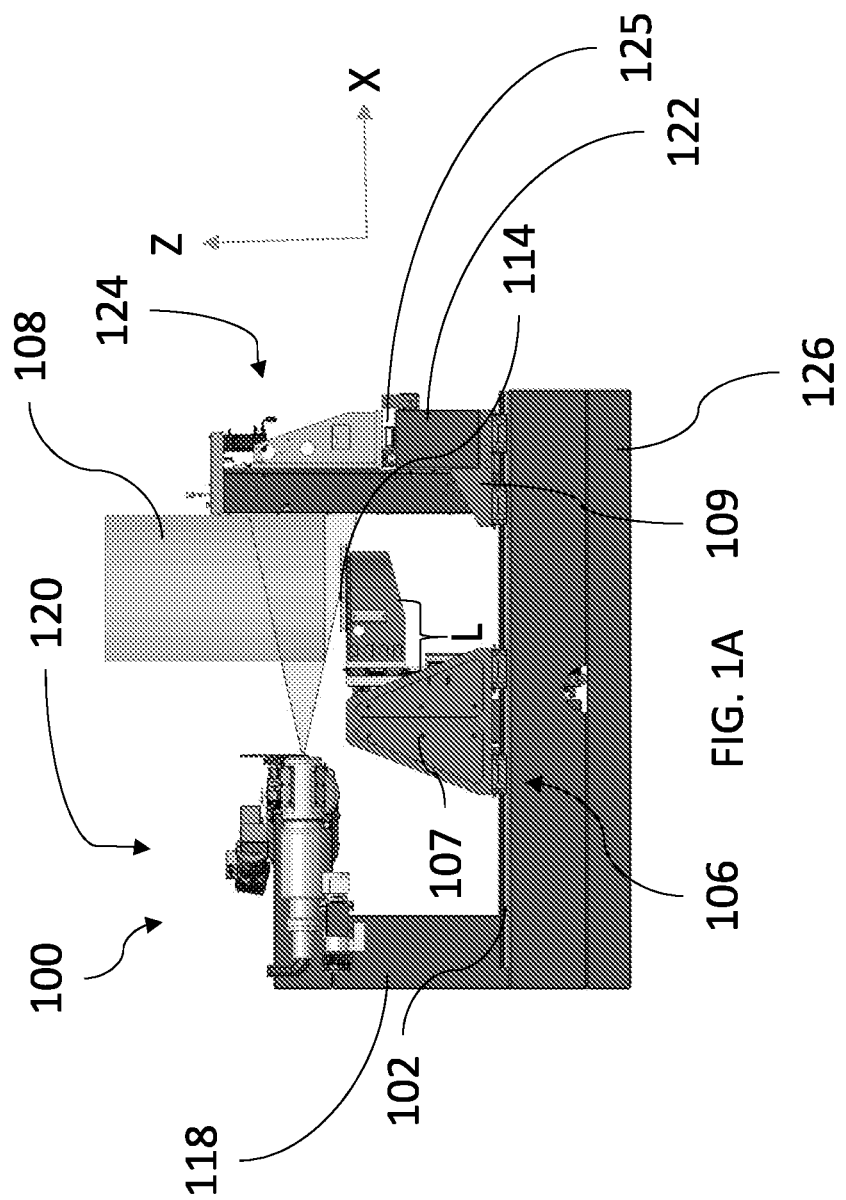

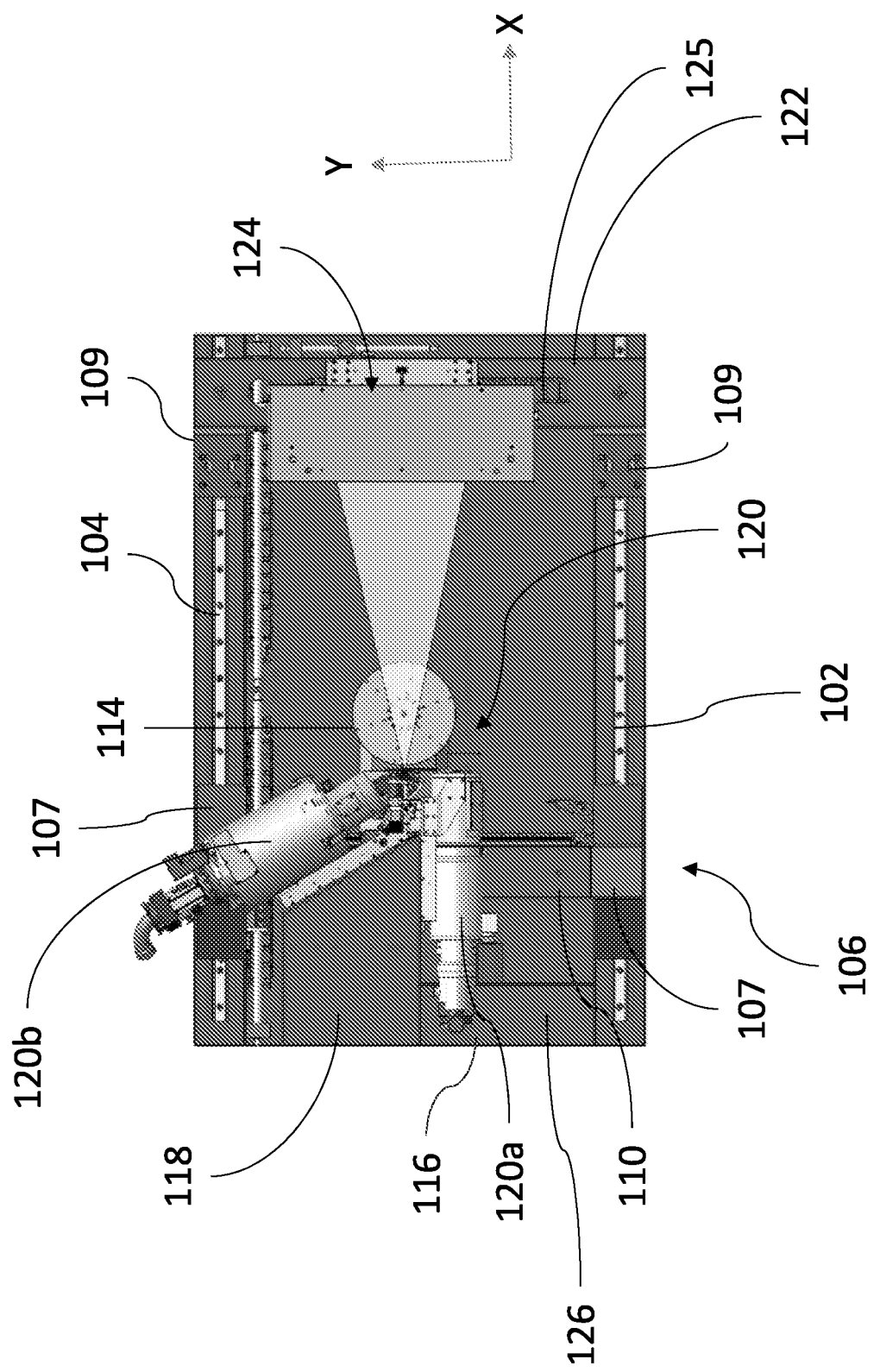

X-RAY SHIELDING CABINET

TECHNICAL FIELD

The disclosure relates to technologies for inspection of larger and heavier parts with very high precision scanning systems.

BACKGROUND

Components, parts, and/or samples sometimes need to be inspected with x-rays or similar inspection techniques. In such instances, inspections are conducted within a controlled environment, for example with a dedicated scanner and manipulator within a shielded housing. Such a scanner supports the component, part, or item to be scanned, then moves the component and/or x-ray source and detector relative to one another.

SUMMARY

This disclosure relates to manipulating and inspecting large and heavy components, sometimes within a shielded cabinet.

In one embodiment, a scanning system is provided having first and second parallel rails. A gantry can span between the first and second rails and it can be movable along a length thereof. A vertical track can be mounted to the gantry and can be movable with the gantry. A sample platform can coupled to the vertical track and can be movable along the vertical track. In some embodiments, the sample platform can be configured to be moved vertically along a Z-axis and horizontally along an X-axis and a Y-axis. In some embodiments, a first support can extend between the first rail and the second rail. In such embodiments, the first support can be at a first end of the first rail and a first end of the second rail. A second support can extend between the first and second rails and can be at a second end of the first rail and a second end of the second rail. In some embodiments, a housing can surround the scanner.

In other aspects, the first support can include a tower extending vertically. The tower can have a height greater than (e.g., taller than) a height of the gantry. An x-ray tube can be mounted to the tower. In some embodiments, the x-ray tube is a first x-ray tube, and the system can further include a second x-ray tube mounted to the tower. The first x-ray tube and the second x-ray tube can be in a same horizontal plane. In some embodiments, the first x-ray tube can be parallel to the first rail and the second rail, and the second x-ray tube can be 40 degrees from parallel with the first rail and the second rail. In some embodiments, the gantry is movable underneath the first x-ray tube and the second x-ray tube.

In some aspects, the second support can include a detector mounted on a horizontal track. In such arrangements, the detector can be movable on the horizontal track, and the horizontal track can be parallel and aligned with the second support. The detector can be configured to detect x-rays, emitted from at least one of the first x-ray tube and the second x-ray tube, that have passed through a sample resting atop the sample platform. In some embodiments, the gantry can be a first gantry, and the second support can be a part of a second gantry movable along the first rail and the second rail. In some embodiments, the first gantry can include a span made of stone.

In some embodiments, the sample platform can have sufficient rigidity that deflections of the platform do not affect operations across an entire weight range of samples. In some embodiments, a plate can extend between the first rail and the second rail. Such a plate can be substantially equal length to at least one of the first rail and the second rail.

Various methods for scanning a sample are also provided. In one embodiment, during operation, a sample can be received by the sample platform. A position of the sample platform can be adjusted by the gantry and the vertical track. The sample can be exposed to x-rays from an x-ray tube. The x-rays can be received by a detector opposite the x-ray tube. In such situations, the received x-rays have passed through the sample.

Prior to adjusting the sample platform, the sample platform can receive a sample to be scanned. In some instances, the sample can have a mass between 75 kg and 100 kg. Based on the sample properties, an x-ray tube can be selected from multiple x-ray tubes. A position of the detector can then be adjusted based on the selected x-ray tube. Adjusting can include setting an X-position, a Y-position, and a Z-position of the sample platform. During scanning, a height of the sample can be adjusted, and the sample can be rotated, while the detector receives the x-rays.

In some embodiments, an x-ray shielding cabinet includes a housing that at least partially defines a cavity configured to receive and retain an x-ray scanning system. A first door can partially define a side and top of the cavity. A first track on the housing can support a first end of the first door and a second track on the housing can support a second end of the first door. In some embodiments, the first door can be moved along the first track and the second track. In some embodiments, a second door partially defines a side and top of the cavity. In such embodiments, a third track on the housing can support a first end of the second door, and a fourth track on the housing can support a second end of the second door. In some embodiments, the fourth track can be parallel to the first track, the second track, and the third track. In some embodiments, the second door can be moved along the third track and the fourth track. The first and second doors can be configured to travel across one another when moving between an open position and a closed position.

In some embodiments, the first door and the second door include one or more of the following features. In some embodiments the first door and the second door can overlap, for example by substantially 125 mm (within standard manufacturing tolerances) when the first door and the second door are both in the closed position. In some embodiments the first door and/or the second door can be L-shaped. Similarly, in some embodiments, the first door and/or the second door can be removable from the housing. Regardless of the shape or removability of each door, in some embodiments, an interface between the first door and the housing can include a labyrinth shield defined by the first door and the housing. Similarly, an interface between the second door and the housing can include a labyrinth shield defined by the second door and the housing in some embodiments. In some configurations, substantially 64%(+ or −5%) a length of the housing can be open when either the first door or the second door is in an open position.

In operation, the first door by can be received the first track and the second track positioned on an x-ray shielding cabinet. Similarly, the second door can be received by the third track and a fourth track. In some instances, the first door can be moved between an open position and a closed position by a motor. Similarly, in some instances, the second door can be moved by a motor between an open position and the closed position. Regardless of which door moves, in some embodiments, either the first door or the second door, in the open position, overlaps a majority of the other door. In operation, at least a portion of x-rays can be blocked by a labyrinth shield defined by the first door and the cabinet or by the second door and the cabinet.

BRIEF DESCRIPTION OF THE FIGURES

The accompanying drawings, which are incorporated in and constitute a part of this disclosure, show certain aspects of the subject matter disclosed herein and, together with the description, help explain some of the principles associated with the disclosed implementations.

FIG. 1A is a side view of an example x-ray scanning device

FIG. 1C is a top-down view of an example x-ray scanning device of FIG. 1A;

DETAILED DESCRIPTION

Figure 1B:
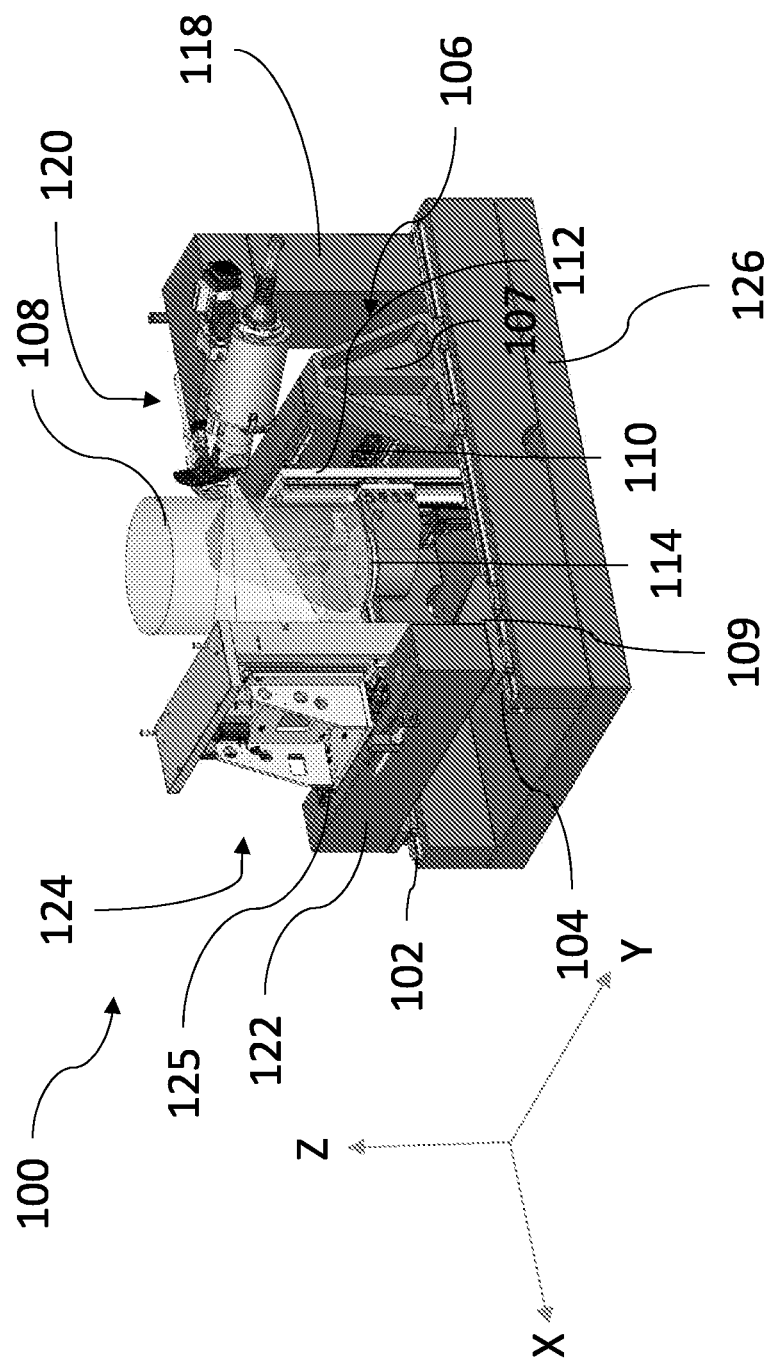
FIG. 1B is a perspective view of the example x-ray scanning device of FIG. 1A.

Certain embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting embodiments and that the scope of the present invention is defined solely by the claims. The features illustrated or described in connection with one embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Scanning large and heavy items (items too large and heavy for a single person to safely place within a scanner) can be difficult. Depending on the scanner design, members of the scanning device can deflect during scanning to the point that the deflection interferes with scanning operations. Similarly, many cabinet designs limit the size of scannable samples as the cabinets define the openings through which the samples are received.

Accordingly, a scanning system is provided, along with a cabinet configured to retain and shielding the scanner. The scanner itself includes first and second parallel rails with a gantry spanning between the rails. The gantry can be movable along a length of the first and second rails. A vertical track can be mounted to the gantry and it can be movable with the gantry. A sample platform can coupled to the vertical track and it can be movable along the vertical track. In some embodiments, the sample platform can be configured to be moved vertically along a Z-axis and horizontally along an X-axis and a Y-axis. For example, in some configurations, the gantry with the sample platform mounted thereto can be configured to move horizontally along the X-axis. The system can also include first support extending between the first rail and the second rail. In such embodiments, the first support can be at a first end of the first rail and a first end of the second rail. The system can also include a second support extending between the first rail and the second rail. The second support can be at a second end of the first rail and a second end of the second rail.

As indicated above, a cabinet is also provided. In some embodiments, an x-ray shielding cabinet includes a housing that at least partially defines a cavity configured to receive and retain an x-ray scanning system. A first door can partially define a side and top of the cavity. A first track on the housing can support a first end of the first door and a second track on the housing can support a second end of the first door. In some embodiments, the first door can be movable along the first track and the second track. In some embodiments, a second door partially defines a side and top of the cavity. In such embodiments, a third track on the housing can support a first end of the second door, and a fourth track on the housing can support a second end of the second door. In some embodiments, the fourth track can be parallel to the first track, the second track, and the third track. In some embodiments, the second door can be movable along the third track and the fourth track. The first and second doors can be configured to travel across one another when moving between an open position and a closed position.

FIGS. 1A, 1B, and 1C illustrate one exemplary embodiment of an x-ray scanning system 100. As shown, the illustrate system 100 includes a first rail 102 and a second rail 104 that extend parallel to one another. A gantry 106 spans, or extends, between the first rail 102 and the second rail 104 and is supported by the first rail 102 and the second rail 104 at both ends of the gantry 106. Having support at both ends can, in some instances, provide improved stiffness and reduced deflection when compared to being supported at a single end. The gantry 106 is movable along the first rail 102 and the second rail 104 and is configured to be sufficiently stiff as to reduce deflections under heavy loads, for example, with a heavy sample 108. In some embodiments, the gantry 106 can include a stone span 110 for such rigidity. The span 110 can be constructed of other sufficiently stiff materials without departing from this disclosure. The span 110 extends between two carts 107 that are configured to along the first rail 102 and the second rail 104. In some embodiments, the carts can be laterally retained to the first rail 102, and/or the second rail 104, being movable only along the X-axis.

A vertical track 112 can be coupled to the span 110. The vertical track 112 is movable with the gantry 106 and along the span 110 of the gantry 106. For example, in some embodiments, the vertical track can be coupled to a motor, such as a stepper motor or servo motor, and a rack arranged to move the vertical track 112 along the span 110. Alternatively or in addition, a worm gear arrangement can similarly be used. For example, direct linear motors, belt systems, or rack and pinion systems can be used without departing from this disclosure. A sample platform 114 is coupled to the vertical track 112 and is configured to move along the vertical track 112. For example, in some embodiments, the sample platform 114 can be coupled to a motor and a rack arranged to move the sample platform 114 along the vertical track 112. Alternatively or in addition, a worm gear arrangement can similarly be used. For example, direct linear motors, belt systems, or rack and pinion systems can be used without departing from this disclosure. Regardless of the movement mechanism, the sample platform 114 can move vertically along a Z-axis by the vertical track, along a Y-axis, perpendicular to the Z-axis, by the vertical track being movable across the span 110, and along the X-axis, perpendicular to both the Z-axis and the Y-axis, by the gantry 106.

Focusing on the sample platform 114, the sample platform 114 can have sufficient rigidity such that deflections of the platform 114 do not affect operations across an entire weight range of samples. This can be achieved by constructing the platform to have a relatively short offset relative to other x-ray scanners, reducing a cantilever length "L". The cantilever length also does not change as the gantry 106 and vertical track 112 move the sample platform along the X-axis and the Y-axis. The sample platform 114 can also be configured to rotate about the Z-axis. Such rotation can be performed by a motor within the sample platform. The rotatable sample platform 114 has sufficient torque to rotate the sample 108 across a wide range of masses, for example, 75 kilograms (kg) to 100 kg. Similarly, such mass can be moved along the X-axis, the Y-axis, and the Z-axis.

Moving to a first end of the system 100, a first support 116 can extend between the first rail 102 and the second rail 104. In some embodiments, the first support 116 can include a rectangular span or a truss. In some embodiments, the first support 116 can include and/or support a tower 118 extending vertically and having a height greater than a height of the gantry 106. Atop the tower 118 can be one or more x-ray tubes 120. For example, in the illustrated embodiment, a first x-ray tube 120a and a second x-ray tube 120b are mounted in a same horizontal plane. Having a first x-ray tube 120a and a second x-ray tube can be useful for a variety of reasons, for example, in some embodiments, the first x-ray tube and the second x-ray tube 120b can have different power ratings. In some embodiments, the first x-ray tube 120a and the second x-ray tube 120b can have different focal lengths. In some embodiments, he first x-ray tube 120a and the second x-ray tube 120b can be different sizes. In the illustrated example, the first x-ray tube 120a is parallel to the first rail 102 and the second rail 104 while the second x-ray tube 120b is 40 degrees from parallel with the first rail 102 and the second rail 104. Regardless of the number of x-ray tubes or the orientation of the x-ray tubes, in some embodiments, the gantry 106 is movable underneath the x-ray tubes 120. This allows for a wider range of sample sizes to be scanned by the system 100.

Looking to the second end of the system 100, a second support 122 extends between the first rail 102 and the second rail 104. In some embodiments, the second support 122 can include a rectangular span or a truss. The second support 122 can support a detector 124 mounted on a horizontal track 125 that is parallel and aligned with the second support 122. The detector is configured to detect x-rays emitted from at least one of the x-ray tubes 120 that have passed through the sample 108 resting atop the sample platform 114. In some embodiments, the second support 122 acts as a second gantry movable along the first rail 102 and the second rail 104. In such embodiments, the support can rest upon carts 109 at each end of the support. In some embodiments, the carts are coupled to the first rail 102 and the second rail 104 similar to the carts 107 for the gantry 106.

In some embodiments, a base plate 126 can extend between the first rail 102 and the second rail 104. In some embodiments, the base plate 126 can also act as the second support. The base plate 126 can have a length that is substantially equal to a length of at least one of the first rail 102 and the second rail 104. In some embodiments the base plate 126 can be made of stone.

As scanning can be sensitive to vibrations and component deflection, a variety of the components described herein can be made of stiff and/or heavy materials, for example, stone such as granite. For example, in some embodiments, the first support, the second support, the tower, the first rail, the second rail, or the gantry can include stone components. Alternatively or in addition, other rigid materials and/or geometries with sufficient stiffness can be used without departing from this disclosure. For example, in some embodiments, steel can be used.

Figure 2:
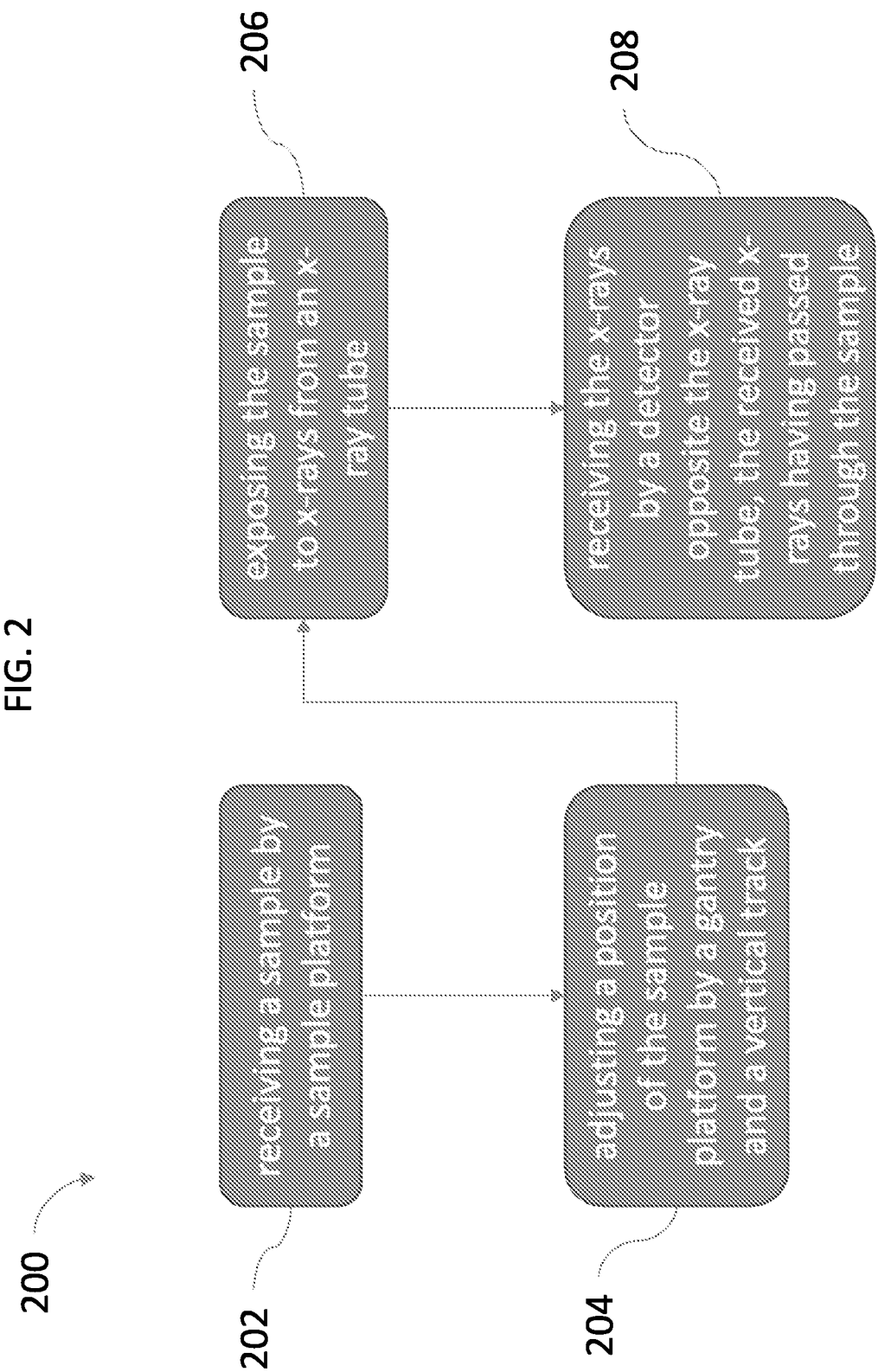
FIG. 2 is flowchart of one embodiment of a method for scanning a sample.

In operation, as shown in FIG. 2, the sample 108 (FIG. 1A-1C) can be received by the sample platform 114 at 202. At 204, a position of the sample platform 114 can be adjusted by the gantry 106 and the vertical track 112. In some instances, adjusting the sample includes setting an X-position, a Y-position, and a Z-position of the sample platform. In some embodiments, an angular position along the Z-axis can be set as well.

In embodiments where multiple x-ray tubes 120 are present, one of the x-ray tubes 120 can be selected for scanning operations. In such embodiments, the position of the detector 124 can then be adjusted based on the selected x-ray tube 120. At 206, the sample 108 is exposed to x-rays from an x-ray tube 120. At 208, the x-rays pass through the sample 108 and are received by the detector 124 opposite the x-ray tube 120. While the x-rays pass through the sample 108 and are received by the detector 124, in some instances, the sample 108 can be rotated. Alternatively or in addition, a height of the sample platform and the sample can be adjusted while exposing the sample to x-rays and while receiving the x-rays by the detector 124.

Figure 3:
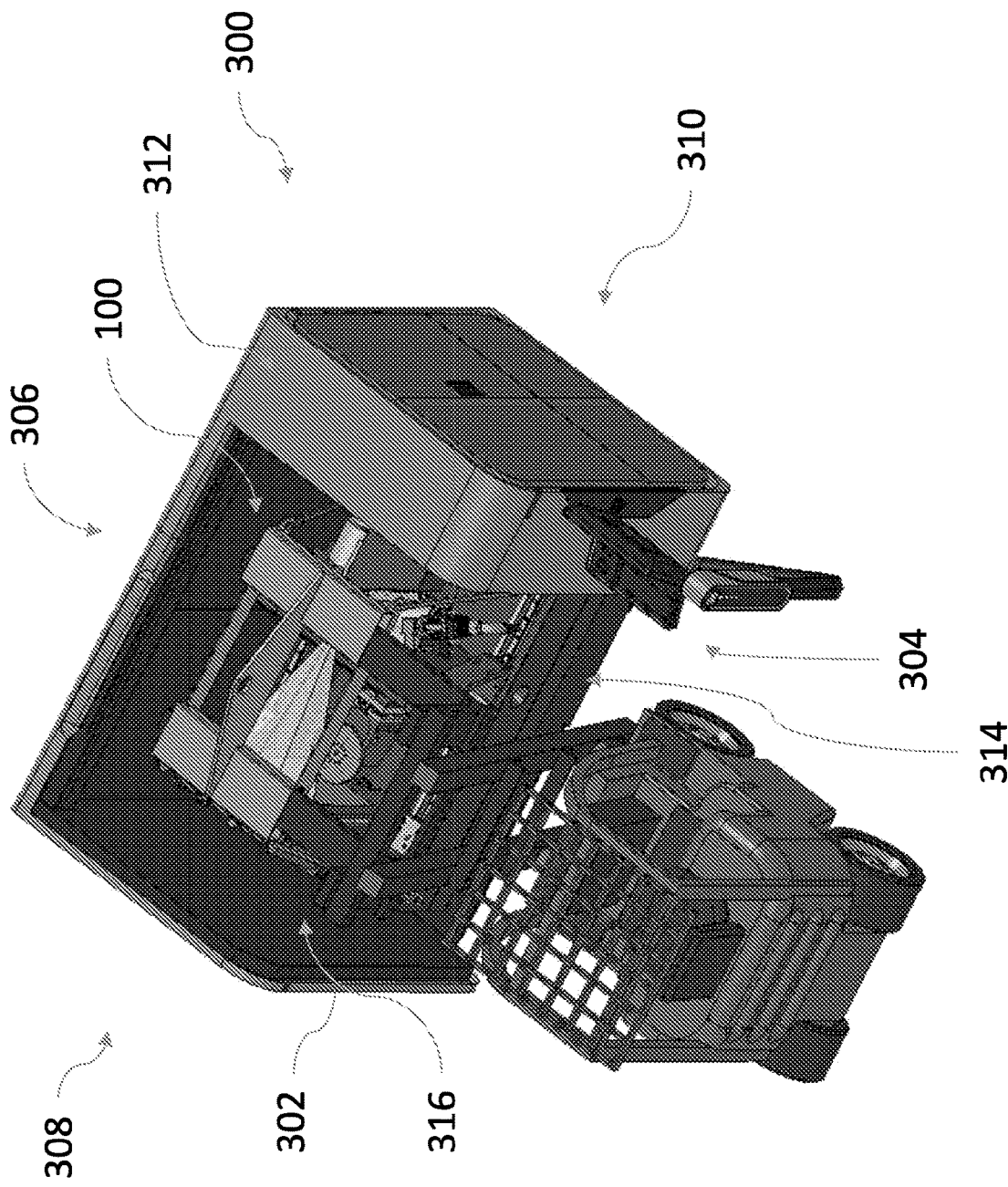
FIG. 3 is a perspective view of the x-ray scanning device of FIG. 1A being placed within one embodiment of a shielded cabinet that has two access door removed.

As scanning operations involve high doses of radiation, a cabinet capable of shielding operators from radiation exposure may be required. FIG. 3 illustrates the x-ray system 100 being placed in such a cabinet 300. The illustrated cabinet 300 includes a housing 302 at least partially defining a cavity configured to receive and retain an x-ray scanning system 100. The housing 302 has a generally rectangular configuration, with front 304, back 306, left 308, and right 310 sidewalls, as well as a top 312 and bottom base 314. However, as shown in FIG. 3, a portion of the front and top walls can define an opening 316 to provide access into the cavity. The housing 302 can further includes shielding, such as lead sheets, within the walls that are potentially exposed to radiation. The cabinet 300 can also include removable doors or panels (removed in FIG. 3) positioned within the opening 316 to ease egress and ingress of the scanner system 100.

Figure 4A:
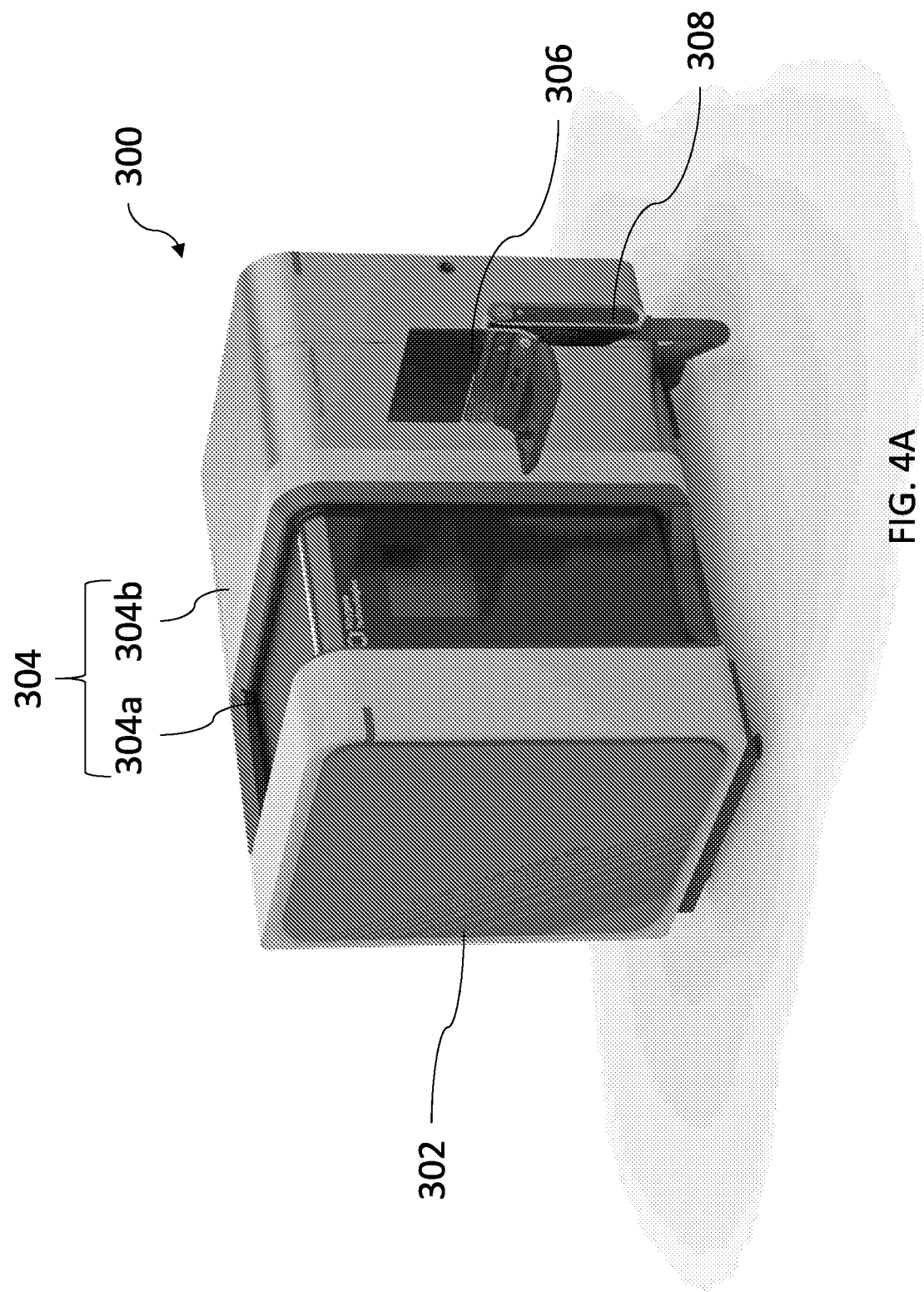
FIG. 4A is a perspective view of the cabinet of FIG. 3 with both a sample door and a maintenance door installed.

FIG. 4A illustrates the cabinet with the doors 304 installed. A first sample door 304a partially defines a side and a top of the cavity while a second maintenance door 304b also partially defines a side and a top of the cavity. To achieve this, in some implementations, both doors can be L-shaped. Alternatively or in addition, U-shaped doors can also be used without departing from this disclosure. Both the sample door 304a and the maintenance door 304b are configured to be supported by the housing 302. The sample door 304a can be arranged and configured to travel across the maintenance door 304b when moving between an open position and a closed position (shown). Similarly, the maintenance door 304b can be arranged and configured to travel across the sample door 304a when moving between an open position and a closed position (shown). In other words, the sample door 304a and the maintenance door 304b are configured to travel across one another when moving between an open position and a closed position. In embodiments where the doors 304 could be exposed to radiation, the doors 304 can include internal radiation shielding, such as lead sheets. To provide adequate shielding, the doors can overlap by a certain amount, e.g., by substantially 60-100 millimeters, and more preferably 125 millimeters (within standard manufacturing tolerances) when the maintenance door 304b and the sample door 304a are both in the closed position.

In some embodiments a controller interface 306 can be attached to the cabinet 300. The control interface can be used to actuate parts of the scanning system 100 within the cabinet 300. Alternatively or in addition, the controller interface 306 can be used to direct the sample door and/or the maintenance door to transition between open and closed positions. In some embodiments, the control interface 306 is mounted on a swivel arm 308. This allows the controller interface 306 to be moved away from the doors 304 for easier access into the cavity. Alternatively or in addition, the scanning system 100 and/or the cabinet can be controlled remotely, for example, from a control room.

Figure 4B:
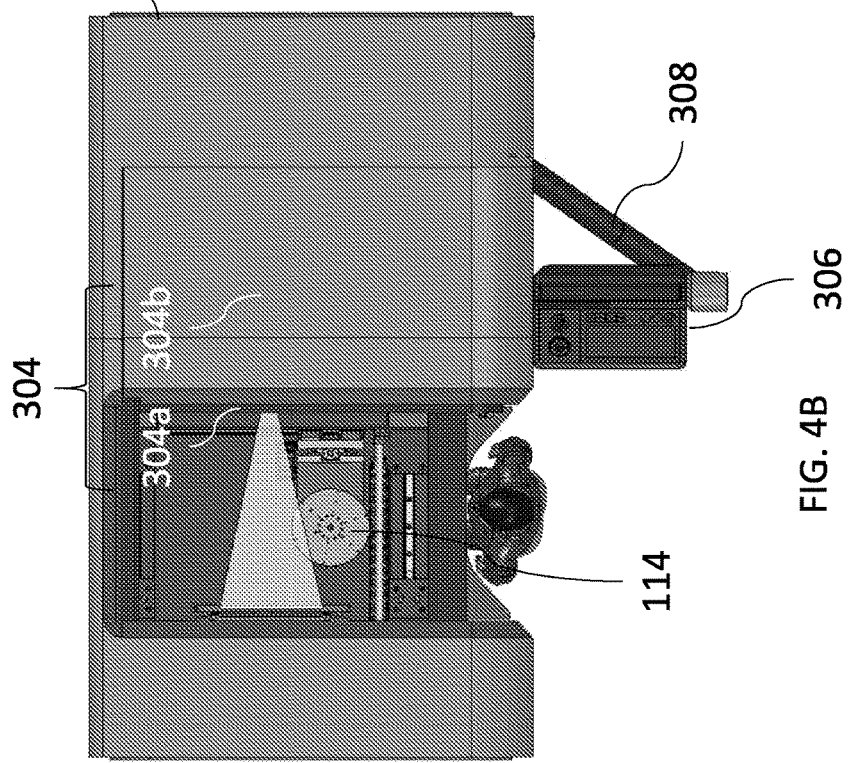
FIG. 4B is a top-down view of the cabinet of FIG. 3 with a sample door in an open position.
Figure 4C:
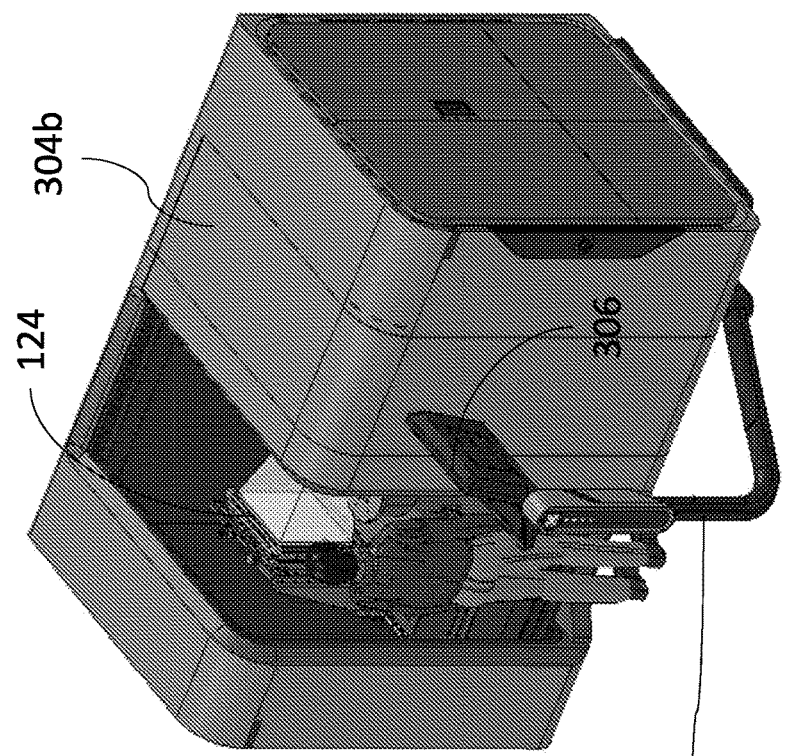
FIG. 4C is a perspective view of the cabinet of FIG. 3 with a sample door in an open position.

The sample door 304a is shown in the open position in FIGS. 4B-4C. The sample door 304a is arranged to allow ingress and egress of samples onto the sample platform 114 of the scanning system 100. As samples 108 can be quite large and/or heavy, the sample door 304a allows access to the cavity, and the sample platform 114 within the cavity, along both a side and top of the cabinet. Such an opening allows for heavy samples to be lowered onto the sample platform 114 by machinery, such as a crane or robotic arm. Side access also allows the sample 108 to be manipulated while the sample 108 is being placed on the sample platform 114 or after the sample 108 has been placed.

Figure 4D:
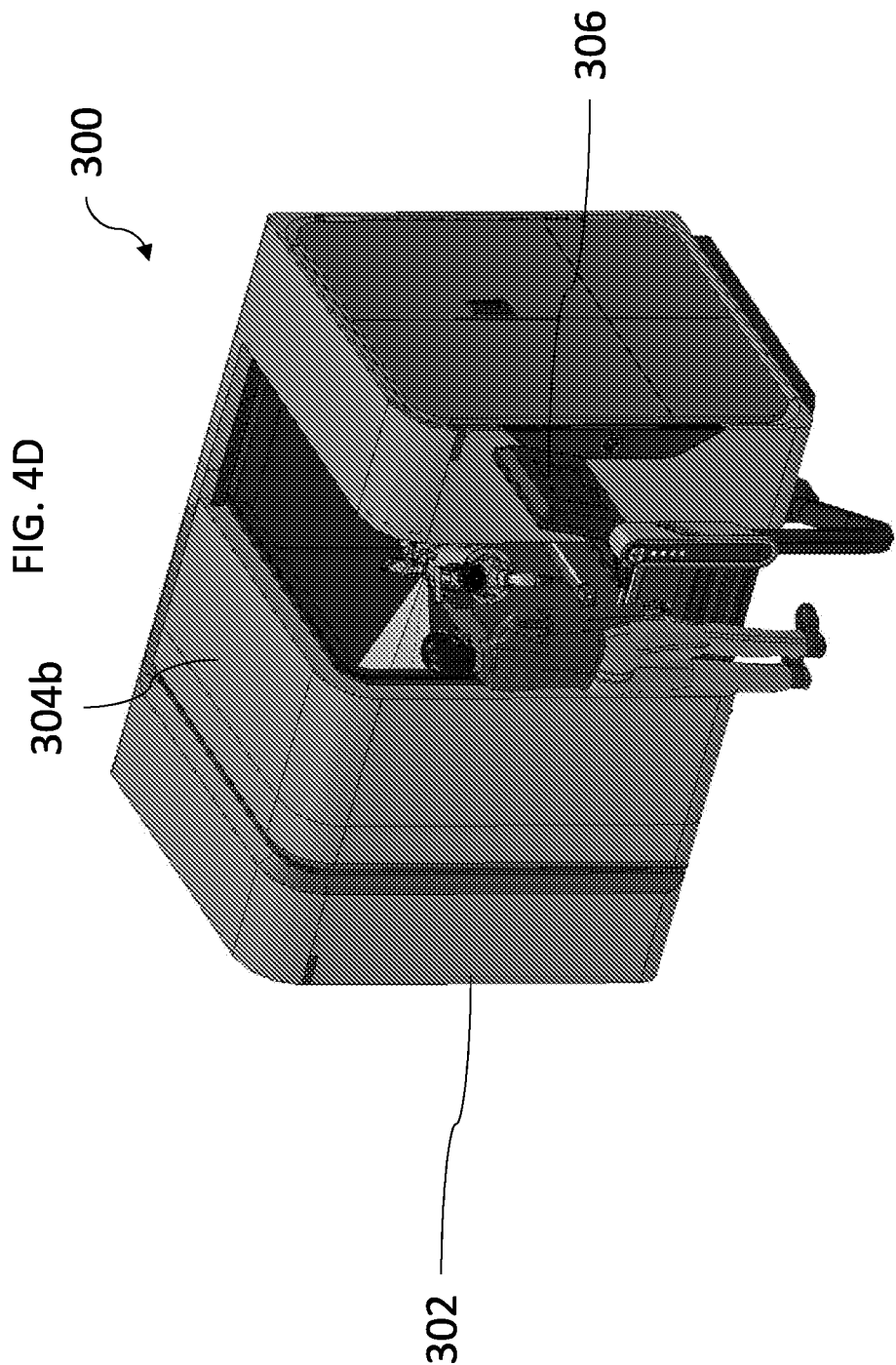
FIG. 4D is a perspective view of the cabinet of FIG. 3 with an maintenance door in an open position.

The maintenance door 304b is shown in the open position in FIG. 4D. The maintenance door 304b is arranged to allow access to components of the scanning system 100 for maintenance and repair, for example, the first x-ray tube 120a and the second x-ray tube 120b. These x-ray tubes 120 can be swapped out based on the sample being scanned or based on maintenance schedules. Other components, such as the gantry may also be accessed through the maintenance door 304b.

Both the maintenance door 304b and the sample door can offer wide openings for easy access for example, in some embodiments, at least 50%, and more preferably about 64% of a length of the housing can be exposed or open when either the maintenance door 304b or the sample door 304a are in an open position. Further assisting with access, as previously described, both doors 304 can be removable from the housing 302. The opening exposed by removing both doors is sufficient to allow the scanning system 100 to be removed or received from the cabinet 300 in a single unitary piece.

Figure 5B:
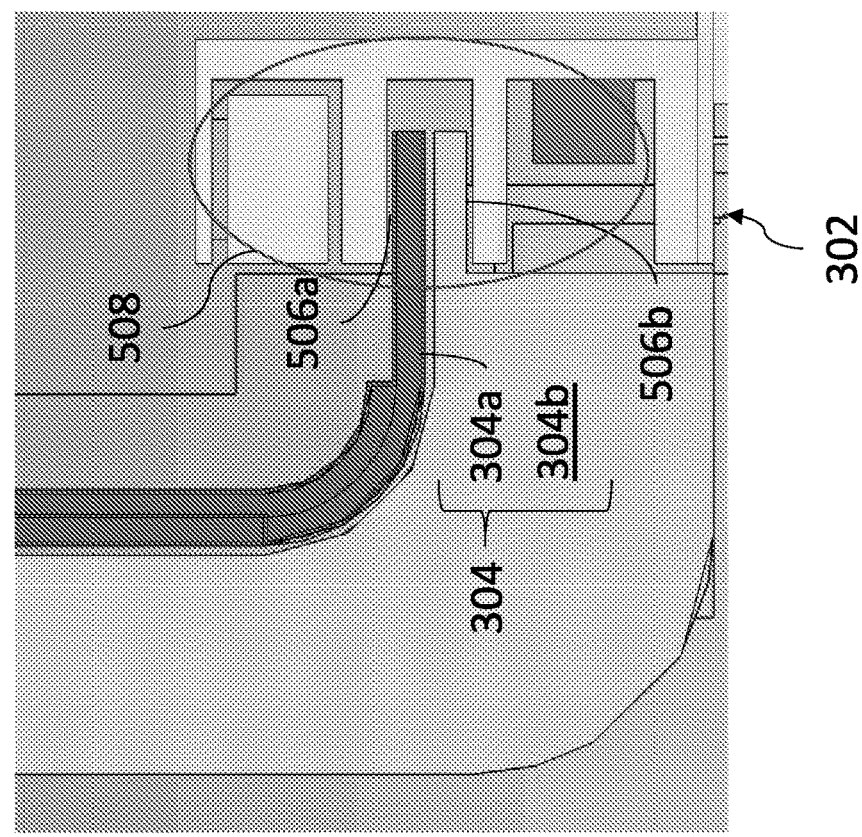
FIG. 5B is a side cross-sectional view of an interface between the lower end of the doors and the housing.
Figure 5A:
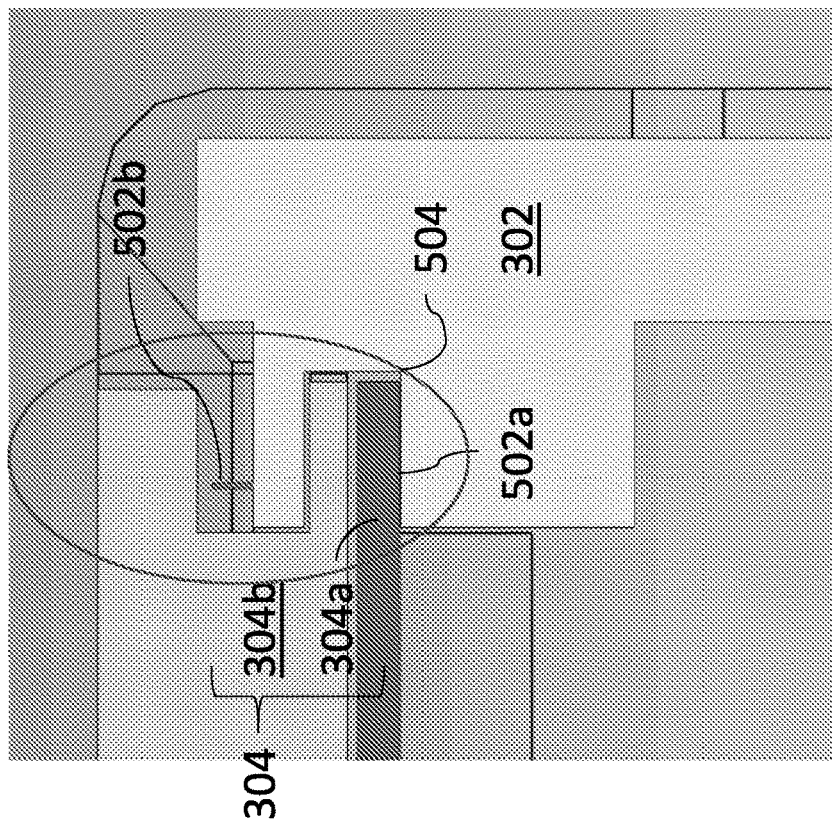
FIG. 5A is a side cross-sectional view of an interface between a upper end of the doors and the housing.

The doors 304 themselves interface with the housing, as shown in FIG. 5A and FIG. 5B, at tracks along each end of the doors 304. In the illustrated cross section, the maintenance door 304b and the sample door 304a are both pictured. In some embodiments, an upper maintenance track 502b can support an upper end of the maintenance door 304b to the housing 302. Similarly, an upper sample track 502a can support an upper end of the sample door 304a to the housing 302. In some embodiments, the upper sample track 502a and the upper sample track 502b can be located near an upper edge of the back sidewall 306. In some embodiments, a labyrinth shield 504 (for example, overlapping shielding sections) can be defined by the maintenance door 304b, the sample door 304a, the housing 302, or a combination. For example, along the upper tracks (502a, 502b), the housing 302 can define two overlapping shielded sections and the maintenance door can define two overlapping sections to form the labyrinth shield.

A lower end of the maintenance door 304b and the sample door 304a similarly can include a lower maintenance track 506b and a lower sample track 506a. In some embodiments, a lower maintenance track 506b can support a lower end of the maintenance door 304b to the housing 302. Similarly, a lower sample track 506a can support a lower end of the sample door 304a to the housing 302. In some embodiments, the lower sample track 506a and the lower maintenance track 506b can be located near a front edge of the cabinet base 314. The tracks (502a, 502b, 506a, 506b) described throughout this disclosure can include roller tracks, slider tracks, or any other type of tracks. In some embodiments, the tracks (502a, 502b, 506a, 506b) can all be parallel to one another. In some embodiments, a motor can be coupled to one or more of the tracks. In such embodiments, the motor can be used to move one or both doors between an open position and a closed position. Similar to an upper end of the doors 304, the lower end of the doors 304 can interface with a lower labyrinth shield 508. For example, along the lower tracks (506a, 506b) the housing can define two overlapping shielded sections to form the labyrinth shield 508.

In use, as indicated above a scanning system, such as system 100, can be positioned in the cabinet with the doors removed. The first door can then be mounted on the first and second tracks. In some embodiments, the lower door, that is, the door that travels underneath the other door, is the first door received. While primarily illustrated as the sample door 304a being the lower door and the maintenance door 304b being the upper door, the opposite can be the case without departing from this disclosure. The second door can then be mounted on the third and fourth tracks. In some embodiments, the upper door, that is, the door that travels over the other door, is the second door received. The third track and the fourth track being parallel to each other and to the first track and the second track.

Once the doors 304 are mounted on their respective tracks, in operation, the doors 304 can be moved between open and closed positions. For example, in some instances, the sample door 304a can be moved between an open position and a closed position. Similarly, in some instances, the maintenance door can be moved between an open position and a closed position. Such movement of either the sample door or the second door can be accomplished by a system operator or a motor built into the cabinet 300. Regardless of how the motion is achieved, when the upper door in the open position, the upper door can overlap a majority of the lower door, for example, over at least about 90% of the lower door. Similarly, when the lower door is in the open position, the lower door can have a majority of the lower door covered by the upper door, for example, at least about 90% of the lower door. When both doors are in the closed position, during scanning operations, x-rays can be blocked by a labyrinth shield (504, 508) defined by the sample door 304a and the cabinet 300 or by the maintenance door 304b and the cabinet 300.

While this disclosure contains many specific embodiment details, these should not be construed as limitations on the scope of what may be claimed, but rather as descriptions of features specific to particular embodiments. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

Other embodiments can be within the scope of the following claims.

What is claimed is:

1. An x-ray shielding cabinet comprising:
   a housing at least partially defining a cavity configured to receive and retain an x-ray scanning system;
   a first door partially defining a side and top of the cavity;
   a first track on the housing supporting a first end of the first door;
   a second track on the housing supporting a second end of the first door, the first door being movable along the first track and the second track;
   a second door partially defining a side and top of the cavity;
   a third track on the housing supporting a first end of the second door; and
   a fourth track on the housing supporting a second end of the second door, the fourth track being parallel to the first track, the second track, and the third track, the second door being movable along the third track and the fourth track;
   wherein a first open position is defined when the first door is moved to a location underneath the second door;
   wherein a second open position is defined when the second door is moved to a location overlapping the first door; and
   wherein the first and second doors are configured to travel across one another when moving between the first open position, the second open position, and a closed position.

2. The x-ray shielding cabinet of claim 1, wherein the first door and the second door overlap by substantially 125 mm when the first door and the second door are both in the closed position.

3. The x-ray shielding cabinet of claim 1, wherein the first door and the second door are each L-shaped.

4. The x-ray shielding cabinet of claim 1, wherein the first door and the second door are removable from the housing.

5. The x-ray shielding cabinet of claim 1, wherein an interface between the first door and the housing comprises a labyrinth shield defined by the first door and the housing.

6. The x-ray shielding cabinet of claim 1, wherein an interface between the second door and the housing comprises a labyrinth shield defined by the second door and the housing.

7. The x-ray shielding cabinet of claim 1, wherein substantially 64% a length of the housing is open when either the first door or the second door is in an open position.

8. A method comprising:
   receiving a first door by a first track and a second track, the first track and the second track being positioned on an x-ray shielding cabinet, the first track and the second track being parallel to one another; and
   receiving a second door by a third track and a fourth track, the third track and the fourth track being parallel to each other and to the first track and the second track;
   moving the first door, by a motor, between a first open position and a closed position, wherein the first door in the first open position is located underneath the second door; and
   moving the second door, by the motor, between a second open position and the closed position, wherein the second door in the second open position overlaps the first door.

9. The method of claim 8, wherein the first door and the second door overlap by substantially 125 millimeters when both the first door and the second door are each in a closed position.

10. The method of claim 8, further comprising blocking x-rays by a labyrinth shield defined by the first door and the cabinet or by the second door and the cabinet.

11. A system comprising:
    an x-ray scanner; and
    an x-ray shielding cabinet comprising:
       a housing at least partially defining a cavity configured to receive and retain an x-ray scanning system;
       a first door partially defining a side and top of the cavity, the first door configured to be supported by the housing;
       a second door partially defining a side and top of the cavity, the second door configured to be supported by the housing, wherein the first door is configured to travel across the second door when moving between a first open position and a closed position, wherein the second door is configured to travel across the first door when moving between a second open position and the closed position, wherein the first open position is defined when the first door is moved to a location underneath the second door, and wherein the second open position is defined when the second door is moved to a location overlapping the first door.

12. The system of claim 11, wherein the first door and the second door overlap by substantially 125 mm when the first door and the second door are both in the closed position.

13. The system of claim 11, wherein the first door is L-shaped.

14. The system of claim 11, wherein the second door is L-shaped.

15. The system of claim 11, wherein the first door is removable from the housing.

16. The system of claim 11, wherein the second door is removable from the housing.

17. The system of claim 11, wherein an interface between the first door and the housing comprises a labyrinth shield defined by the first door and the housing.

18. The system of claim 11, wherein an interface between the second door and the housing comprises a labyrinth shield defined by the second door and the housing.

* * * * *